United States Patent [19]

Wilkins

[11] 4,440,175

[45] Apr. 3, 1984

[54] MEMBRANE ELECTRODE FOR NON-IONIC SPECIES

[75] Inventor: Ebtisam Wilkins, Albuquerque, N. Mex.

[73] Assignee: University Patents, Inc., Norwalk, Conn.

[21] Appl. No.: 291,737

[22] Filed: Aug. 10, 1981

[51] Int. Cl.$^3$ .............................................. A61B 5/00
[52] U.S. Cl. ..................................... 128/635; 435/15; 204/400
[58] Field of Search ............................... 128/632, 635; 204/195 R, 195 B, 195 M, 1 T; 436/95, 150, 68; 422/68

[56] References Cited

U.S. PATENT DOCUMENTS 3,966,580 6/1976 Janata et al. .................... 204/195 B
4,115,209 9/1978 Freiser et al. ................... 204/195 M
4,260,680 4/1981 Maramatsu et al. ............. 204/195 B Primary Examiner—Benjamin R. Padgett
Assistant Examiner—T. J. Wallen
Attorney, Agent, or Firm—George M. Yahwak

[57] ABSTRACT

Concentrations of non-ionic species in aqueous media are measured as a function of potentiometric or polarographic response, employing a membrane electrode selective for the non-ionic species being measured. The electrode comprises a conductive substrate and a membrane formed as a layer on the conductive substrate and adapted for interfacing with the aqueous medium. The membrane is composed of a polymeric matrix having dispersed or dissolved therein an anion exchange material and a water-insoluble salt of the non-ionic species being measured. The electrode is particularly suitable for use as an implantable glucose sensor for continuous in vivo monitoring of glucose concentration in the blood or interstitial fluid.

13 Claims, No Drawings

MEMBRANE ELECTRODE FOR NON-IONIC SPECIES

BACKGROUND OF THE INVENTION

This invention relates to membrane electrodes and, more particularly, to electrodes for use in potentiometric or polarographic assays for non-ionic species.

The ability to accurately and rapidly measure the concentration of various non-ionic species in aqueous media is oftentimes critically important, particularly in situations requiring the monitoring of the concentration of a non-ionic component of a patient's blood. A primary example is the need for monitoring blood glucose levels in diabetic patients requiring insulin injections for control of the disease in proper dosage which is dependent upon the blood glucose level.

In diabetic patients, checking for spill of glucose into the urine and spot blood glucose determinations on an out-patient basis may not provide sufficient information to bring glucose back under control. Furthermore, determination of glucose spill into the urine can sometimes lead to an erroneous judgment about the patient's current insulin requirement. To evaluate and successfully treat this patient, the physician must obtain frequent blood glucose determinations. Frequent blood glucose determination is also desirable when a diabetic patient is acutely ill, undergoing major surgery or childbirth, or suffering from severe keto-acidosis.

Numerous attempts to provide a bedside instrument suitable for continuous glucose monitoring have been made. For the most part, these instruments have required withdrawal of a blood sample from the patient's body, and have not been suitable for implantation for continuous in vivo glucose monitoring. While some of these instruments have employed electrochemical sensors for measuring blood glucose concentration as a function of potentiometric or polarographic response, such sensors have relied upon electrochemical systems which provide only an indirect measurement of glucose concentration. Direct electrochemical measurement of glucose concentration has thus far not been possible. The problems encountered with all of these various previously proposed continuous glucose monitoring instruments have included clotting, non-linearity of the signal output, and drift in the blood sampling and detector systems.

The development of an implantable glucose sensor for the continuous in vivo monitoring of glucose concentration in blood or interstitial fluid without the need for withdrawal of body fluids, and which provides a signal which represents a direct measurement of glucose concentration, should lead to a marked improvement in clinical management and scientific understanding of diabetes. The availability of such a sensor with long-term stability could provide a continuous input for an implanted glucose-controlled glucagon and insulin delivery system, thus aiding greatly in re-establishing and maintaining normal blood glucose levels in the acutely uncontrolled diabetic patients. In addition, such a continuous in vivo sensor would make it much more feasible to conduct a study to determine what influence fluctuation of blood glucose concentration may have on the development of the well-known complications of diabetes.

A recently developed type of electrochemical sensor which has many of the characteristics rendering it potentially suitable for implantation and continuous in vivo monitoring of concentrations of various blood components, is a membrane electrode which is commonly referred to as a "coated wire" electrode. Ion-selective coated wire electrodes are described in detail in the Freiser, et al., U.S. Pat. No. 4,115,209 issued Sept. 19, 1978, incorporated herein by reference to the extent that it is pertinent. In the coated wire-type ion-selective membrane electrode, an ion-selective polymeric membrane is formed as a layer on a conductive substrate, for example, by forming the membrane as a coating directly on the conductive substrate, which is typically in the form of a conductive wire, thereby eliminating the internal reference electrode element employed in the more conventional barrel-type membrane electrodes. The ion-selective polymer membrane is composed of a polymeric matrix having dispersed or dissolved therein a suitable ion-exchange material, i.e., a cation exchange material for cation sensitivity, and an anion exchange material for anion sensitivity. By proper selection of the ion exchange material in the membrane component of the electrode, the electrode may be rendered capable of selectively sensing one or more species of cations or anions present in a test solution. The membrane electrodes described by Freiser, et al., are limited in their utility to the measurement of concentrations of ionic species in test solutions, and are not applicable to non-ionic species.

SUMMARY OF THE INVENTION

It is, accordingly, a primary object of the present invention to provide an improved membrane electrode which is capable of measuring the concentration of a non-ionic species in a liquid medium as a function of potentiometric or polarographic response.

Another object of the invention is to provide a membrane electrode in accordance with the preceding object, which is capable of measuring glucose concentrations in aqueous media.

A further object of the invention is to provide a membrane electrode in accordance with the preceding object, which enables a potentiometric or polarographic response which represents a direct measurement of the glucose concentration.

Still another object of the invention is to provide a membrane electrode in accordance with the preceding objects, which is suitable for implantation within the body for continuous in vivo monitoring of glucose concentration in the blood or interstitial fluid.

The above and other objects are achieved in accordance with the present invention, by providing a membrane electrode whose membrane component is selective for a particular non-ionic species and is composed of a polymeric matrix having dispersed or dissolved therein an anion exchange material and a water-insoluble salt of the non-ionic species whose measurement is desired. The membrane is formed as a layer on a conductive substrate and is adapted for interfacing with the liquid medium being assayed.

The membrane electrode of the present invention is particularly suitable for glucose concentration measurement, and provides a potentiometric or polarographic response which represents a direct measurement of the glucose concentration. When the membrane component is formed of a blood-compatible polymeric material, the electrode is suitable for implantation within the body for continuous in vivo monitoring of the concentration of glucose or other non-ionic species in the blood or interstitial fluid.

DESCRIPTION OF PREFERRED EMBODIMENTS

The polymeric matrix of the membrane component of the membrane electrode in accordance with the present invention, may be formed of any suitable polymeric material, including, for example, addition polymers, such as the vinyl polymers, including polyvinyl chloride, polyvinylidene chloride, polyethylene, polypropylene, polybutadiene, polyacrylamides, polyacrylates, polyvinyl acetate, chloroprene, polystyrenes, polyacrylonitrile, and the like; condensation polymers, such as polyamides, polycarbonates, polyurethanes, polyesters, polyethers, and the like; and natural resins such as purified natural rubber. For body implantation, the polymer should be one exhibiting good blood compatibility.

The anion exchange material of the membrane component may suitably be, for example, a quaternary alkyl, aryl, or aralkyl ammonium phosphonium, arsonium, stibonium or sulfonium salt. Preferably, the anion exchange material is a quaternary ammonium salt, such as, for example, tricaprylyl methyl ammonium chloride, commercially available under the trade name Aliquat 336S.

The non-ionic species to be measured must be present in the membrane component of the electrode in the form of a water-insoluble salt thereof. Electrode performance with water-soluble salts has been found to be totally unsatisfactory. The water-insoluble salt is preferably an alkaline earth metal salt, with barium salts having been found to be particularly suitable.

By proper selection of the non-ionic species moiety of the water-insoluble salt, the membrane electrodes of the present invention can be rendered sensitive to any particular non-ionic species whose measurement is desired. While the electrode has been found to be particularly suitable for use in measuring glucose concentration, its applicability extends to a wide range of other non-ionic species, including, for example, fructose, creatine, and creatinine glycogen, and the like.

The membrane will generally include the anion exchange material in amounts ranging from about 1 to about 25% by weight, and preferably from about 10 to about 25% by weight. The molar ratio of the anion exchange material to the water-insoluble salt of the non-ionic species will generally range from about 1:1 to about 3:1, with about 2:1 being preferred. One or more plasticizers for the polymer, compatible with the polymer, the anion exchange material, and the water-insoluble salt, may be included within the membrane to attain a more homogenous mixture of the components thereof. Suitable plasticizers which may be used, alone or in combination, depending upon the particular polymer employed, include cyclohexanone, dioctyl phosphonate, tributyl phosphate, isoamyl alcohol, n-decanol, diphenylphthalate, dioctylphthalate, and diphenylphthalate. When a plasticizer is used, it will generally be employed in an amount ranging from about 10 to about 50% by weight of the membrane.

The membrane may suitably be prepared by first forming a homogenous solution of the polymer, the anion exchange material, the water-insoluble salt of the non-ionic species, and the optional plasticizer, in a suitable organic solvent, such as, for example, an alcohol (e.g., isoamyl alcohol, benzyl alcohol, or decanol), a ketone (e.g., cyclohexanone), an ester (e.g., methyl acetate, or tributyl phosphate), a cyclic ether (e.g., tetrahydrofuran), or mixtures thereof. Such solution is then either cast or coated onto a suitable substrate, depending upon the type of electrode being prepared, and the solvent is then evaporated.

In the membrane electrode of the present invention, the membrane is formed as a layer (e.g., coated or laminated) on a conductive substrate. Any suitable conductive substrate can be employed, such as, for example, platinum, silver, gold, copper, carbon, or the like. Noble metals are particularly suitable as conductive substrates. The membrane is preferably formed as a coating directly on the conductive substrate, which is most conveniently in the form of a fine wire.

Before use, the membrane electrodes of the present invention should suitably be conditioned by soaking in a dilute solution of the non-ionic species for which it is sensitive (e.g., for 2 to 3 hours, depending on the thickness of the membrane), and stored in such conditioning solution when not in use.

The membrane electrodes of the present invention may suitably be employed, in accordance with conventional assaying techniques well known in the art, for direct potentiometric or polarographic assays for measuring the concentration of a given non-ionic species in various aqueous test solutions, including body fluids such as blood, plasma, serum, urine and the like. The electrodes are particularly suitable for use in providing a direct measurement of glucose concentration in blood or other body fluids, and are suitable for being implanted within the body for continuous in vivo monitoring of such glucose concentration. If necessary to achieve a response, the electrode may be biased by an applied small voltage generated by an external source of EMF.

The invention is further illustrated by way of the following examples.

EXAMPLE 1

A barium salt of glucose was synthesized by the addition of 100 ml of 1 M glucose to 50 ml of 1 M $BaCl_2$. The solution was left for two weeks to evaporate slowly. The crystals obtained were then dissolved in 20 ml of a 60% (v/v) solution of tricaprylyl methyl ammonium chloride in decanol, and stirred for two days. Polyvinyl chloride was separately dissolved in a minimal amount of cyclohexanone (5 gm PVC in 12 ml cyclohexanone). The barium glucose salt-quaternary ammonium salt solution and the polymer solution were then mixed in a 1:3 volume ratio. The tip of a thin platinum wire (0.257 mm in diameter) was then dipped twice into the mixed solution, and the solvent then evaporated by air drying at room temperature to form the membrane as a coating on the wire.

The resulting membrane electrode was conditioned before use by soaking in $10_M{}^{-3}$ glucose solution for two to three hours, and stored in this conditioning solution when not in use. The potential differences of the membrane electrode vs. a calomel reference electrode were determined in different concentrations of stagnant glucose solutions made with pH 7.4 phosphate buffer at 37° C., using 600 mv bias.

In both long-term and short-term tests, the membrane electrode was found to exhibit a current response which was linear with the logarithm of glucose concentration over the range of 40–200 mg percent.

EXAMPLE 2

The procedure of Example 1 was repeated, but this time substituting for the barium salt of glucose a water-soluble sodium salt of glucose made from 0.001 M NaOH and glucose pentaacetate (3.9 gm glucose pentaacetate dissolved and diluted to 20 ml with 0.001 M NaOH).

The resulting membrane electrode was found to give a response similar to that of the membrane electrode of Example 1 in short-term tests. However, in the long-term tests, the performance characteristics of this membrane electrode deteriorated to the point of being of no practical use.

I claim:

1. A membrane electrode for use in measuring the concentration of a non-ionic species in an aqueous medium as a function of potentiometric or polarographic response comprising a conductive substrate component and a membrane component layered or coated on said substrate component, said membrane being compatible and non-reactive with the aqueous medium and comprising
   (a) a polymeric material;
   (b) an anion exchange material; and
   (c) a water-insoluble salt of said non-ionic species to be measured.

2. The membrane electrode of claim 1, wherein said non-ionic species is glucose.

3. The membrane electrode of claim 1, wherein said anion exchange material is a quaternary ammonium salt.

4. The membrane electrode of claim 1, wherein said water-insoluble salt is an alkaline earth metal salt.

5. The membrane electrode of claim 4, wherein said alkaline earth metal is barium.

6. The membrane electrode of claim 5, wherein said non-ionic species is glucose, and said anionexchange material is a quaternary ammonium salt.

7. The membrane electrode of claim 1, wherein said conductive substrate is a noble metal.

8. The membrane electrode of claim 7, wherein said conductive substrate is in the form of a conductive wire.

9. The membrane electrode of claim 1 wherein the anion exchange material is present in amounts of from about 1 to about 25 percent of said membrane component, and wherein the molecular ratio of the anion exchange material to the water insoluble salt is from about 1:1 to about 3:1.

10. In a process for the measurement of glucose concentration in an aqueous medium as a function of potentiometric or polarographic response which represents a direct measurement of said glucose measurement which comprises the insertion of an electrode into the aqueous medium containing an amount of dissolved glucose, the improvement which comprises utilizing an electrode comprising a conductive substrate component and a membrane component layered or coated on said substrate component, said membrane being compatible and non-reactive with the aqueous medium and comprising (a) a polymeric material, (b) an anion exchange material, and (c) a water-insoluble salt of glucose.

11. The process of claim 10, wherein said aqueous medium is a body fluid.

12. The process of claim 11, wherein said body fluid is blood.

13. The process of claim 11, wherein said membrane electrode is implanted within the body for continuous in vivo monitoring of glucose concentration in the blood or interstitial fluid.

* * * * *